United States Patent [19]
De Lacharriere et al.

[11] Patent Number: 5,895,649
[45] Date of Patent: Apr. 20, 1999

[54] METHOD FOR TREATING NEUROGENIC RED SKIN BLOTCHES WITH COMPOSITIONS CONTAINING TNF-ALPHA ANTAGONISTS

[75] Inventors: Olivier De Lacharriere, Paris; Lionel Breton, Versailles, both of France

[73] Assignee: Societe L'Oreal S.A., Paris, France

[21] Appl. No.: 08/752,551

[22] Filed: Nov. 20, 1996

[30] Foreign Application Priority Data

Nov. 20, 1995 [FR] France ................................ 95 13729

[51] Int. Cl.$^6$ ................ A61K 39/395; A61K 35/12; A61K 35/78; A61K 31/18
[52] U.S. Cl. ................ 424/130.1; 424/195.1; 424/520; 514/2; 514/263; 514/338; 514/557; 514/588; 514/738; 514/886; 514/887; 514/937; 514/938
[58] Field of Search ................ 424/195.1, 520, 424/130.1; 514/263, 338, 2, 557, 738, 588, 886, 887, 937, 938

[56] References Cited

FOREIGN PATENT DOCUMENTS 0680749  11/1995  European Pat. Off. ......... A61K 7/48

OTHER PUBLICATIONS

Gallin, In Fundamental Immunology, Third Edition, Ed., W.E. Paul, Raven Press, Ltd., NY, pp. 1015–1032, 1993.
J. Invest. Dermatol., vol. 102, No. 6, 1994, pp. 934–937, XP000576630, G. Senaldi et al.: "Protective effect of N-acetylcysteine in hapten-induced irritant and contact hypersensitivity reactions".

J. Exp. Med., vol. 173, No. 3, 1991, pp. 673–679, XP000576859, P.F. Piguet et al.; "Tumor necrosis factor is a critical mediator in hapte–induced irritant and contact hypersensitivity reactions".

Agents & Actions, vol. 38, No. s.i. II, 1993, pp. C212–C214, XP000576409, N.A. Hayes et al.: "The action of a calcitonin gene–related peptide antagonist in human skin".

Semin. Dermatol., vol. 10, No. 3, 1991, pp. 138–147, XP000576399, J.T. APGAR: "Newer aspects of inflammatory bowel disease and its cutaneous manifestations: a selective review".

Cell. Immunol., vol. 161, No. 2, 1995, pp. 288–294, XP000576633, N. Higashi et al; "Involvement of inflammatory cytokines in a delayed–type hypersensitivity reaction".

*Primary Examiner*—David M. Naff
*Assistant Examiner*—Janet M. Kerr
*Attorney, Agent, or Firm*—Burns, Doane, Swecker & Mathis, L.L.P.

[57] ABSTRACT

Topically applicable pharmaceutical/dermatological/cosmetic compositions, well suited for the therapeutic treatment of neurogenic red skin blotches and rosacea afflicting the skin, scalp and/or mucosae of a human subject, comprise a therapeutically/cosmetically effective amount of at least one TNF-alpha antagonist.

20 Claims, No Drawings

METHOD FOR TREATING NEUROGENIC RED SKIN BLOTCHES WITH COMPOSITIONS CONTAINING TNF-ALPHA ANTAGONISTS

BACKGROUND OF THE INVENTION

1. Technical Field of the Invention

The present invention relates to the formulation of TNF-alpha (tumor necrosis factor alpha) antagonists into topically applicable cosmetic, pharmaceutical and/or dermatological compositions for treating red blotches on the skin of neurogenic origin, and especially for treating rosacea.

2. Description of the Prior Art

Rosacea is a skin affliction or condition characterized by an erythema of the face most prominent on the cheekbones, forehead and nose and a hyperseborrhoea of the face on the forehead, nose and cheeks, and by an infectious component with pustules.

Moreover, these indications are associated with a neurogenic component, namely, a hyperreactivity of the skin of the face and neck, manifested by the appearance of red blotches and of subjective sensations of the itching or pruritus type, sensations of burning or hotness, sensations of prickling, pins and needles, discomfort, twinges, and the like.

These indications of hyperreactivity may be triggered by a wide variety of factors, such as the consumption of food or of hot or alcoholic beverages, by rapid temperature variations, by heat, and in particular exposure to ultraviolet or infrared irradiation, by a low relative humidity, by exposure of the skin to raging winds or to drafts (fans, air-conditioning), and by the application of surfactants or other compounds even when these are not known to be, especially, irritants.

These red blotches, which can persist for several hours after exposure of the skin to the stimulus, are often unsightly and often create significant psychological embarrassment.

Hitherto, the mechanism of the triggering of these indications was very poorly understood, and rosacea was treated with active agents such as antiseborrhoeic and anti-infectious agents, for example benzoyl peroxide, retinoic acid, metronidazole or cyclines, which acted against the infection and the hyperseborrhoea, but which did not therapeutically treat the erythematous component of this affliction or the hyperreactivity of the skin.

Hence, serious need continues to exist for an effective regimen for the treatment of cutaneous red blotches, an essential component of the hyperreactivity condition of the skin affected by rosacea.

SUMMARY OF THE INVENTION

It has now unexpectedly and surprisingly been determined that cutaneous red blotches can be therapeutically treated by topically applying TNF-alpha antagonists thereto.

Hitherto, the use of TNF-alpha antagonists for treating cutaneous red blotches, in particular rosacea, was unknown to this art.

Briefly, the present invention features the formulation of at least one TNF-alpha antagonist into topically applicable cosmetic, pharmaceutical and/or dermatological compositions for treating cutaneous red blotches of neurogenic origin.

The present invention more especially features the formulation of at least one TNF-alpha antagonist into topically applicable cosmetic, pharmaceutical and/or dermatological compositions for treating rosacea.

Topical application of the subject compositions containing one or more TNF-alpha antagonists elicits a marked decrease or even a complete disappearance of the red blotch which manifests itself, in particular, in rosacea.

Too, this invention features a regimen for the cosmetic, dermatological and/or pharmaceutical treatment of neurogenic red blotches of the skin of a human subject afflicted therewith, in particular afflicted with rosacea, comprising topically administering at least one TNF-alpha antagonist, in a cosmetically, dermatologically or pharmaceutically acceptable medium, to the skin, the scalp and/or the mucosae.

DETAILED DESCRIPTION OF BEST MODE AND SPECIFIC/PREFERRED EMBODIMENTS OF THE INVENTION

More particularly according to the present invention, the subject compositions comprise a cosmetically, pharmaceutically or dermatologically acceptable medium, namely, a vehicle, diluent or carrier which is compatible with the skin, nails, mucosae, tissues and hair. The subject compositions containing the at least one TNF-alpha antagonist may be applied topically to the face, neck, hair, mucosae and nails, the major folds or any other cutaneous region of the body.

By "TNF-alpha" antagonist is intended any species or substance capable of inhibiting the release and/or synthesis and/or receptor binding of TNF-alpha.

According to the invention, only one TNF-alpha antagonist can be administered, or, jointly, a plurality thereof.

For a substance to be recognized as a TNF-alpha receptor antagonist, it must exhibit, in particular, the following characteristics:

(a) a selective affinity for the specific TNF-alpha receptors;

(b) pharmacological activity as a TNF-alpha receptor antagonist, namely, inducing a coherent pharmacological response in the following tests: inhibition of the TNF-alpha-induced adhesion of macrophages on endothelial cells, or inhibition of the TNF-alpha-induced liberation of superoxide anions on neutrophils, or inhibition of the mitogenic activity of TNF-alpha on fibroblasts of the dermis.

For a substance to be recognized as an antagonist of the release and/or synthesis of TNF-alpha, it must, in particular, inhibit the release of TNF-alpha by monocytes (U937 cells) which are differentiated using a phorbol ester (PMA).

The TNF-alpha antagonists may be inorganic molecules or synthetic organic molecules, or extracts of natural (plant or animal) materials.

The TNF-alpha receptor antagonists and the inhibitors of the release and/or synthesis of TNF-alpha which are suitable for the present invention include, in particular, lisophylline, A802715, sulphasalazine, CDP-571 (anti-TNF-alpha antibody) and MDL-201112.

In the compositions according to the invention, the TNF-alpha antagonists are preferably incorporated in an amount ranging from 0.000001% to 10% by weight relative to the total weight of the composition, and preferably in an amount ranging from 0.0001% to 5% by weight relative to the total weight of the composition.

Advantageously, the TNF-alpha antagonists are combined with one or more antagonists of one or more neuropeptides and/or one or more antagonists of one or more inflammation mediators.

Exemplary neuropeptide antagonists which are suited for the invention include substance P antagonists and CGRP antagonists. Advantageously, substance P receptor and/or CGRP receptor antagonists are used.

Substance P is a polypeptide chemical species produced and released by a nerve ending. It belongs to the family of tachykinins which originate from the free nerve endings of the epidermis and dermis. Substance P participates, in particular, in the transmission of pain and in disorders of the central nervous system such as anxiety and schizophrenia, in respiratory and inflammatory disorders, in gastrointestinal disorders, in rheumatic disorders and in certain dermatological disorders such as eczema, psoriasis, urticaria and contact dermatitis.

Exemplary substance P antagonists according to the invention include any substance or species of organic or inorganic origin capable of effecting an inhibition of the receptor binding of substance P or an inhibition of the synthesis and/or release of substance P by sensory nerve fibers.

For a substance to be recognized as a substance P antagonist, it must exhibit pharmacological activity as a substance P antagonist, namely, it must induce a coherent pharmacological response, in particular, in one of the following two tests:

(a) the antagonist substance must decrease the extravasation of plasma through the vascular wall induced by capsaicin or by an antidromic nerve stimulation, or, alternatively;

(b) the antagonist substance must cause inhibition of the smooth muscle contraction induced by the administration of substance P.

The substance P antagonist can, in addition, exhibit a selective affinity for the NK1 receptors of tachykinins.

The substance P receptor antagonist can be a peptide or a non-peptide derivative containing a hetero atom. It may also be selected from among salts and from among extracts of plant and/or bacterial origin.

Exemplary substance P receptor antagonist peptides include sendide and spantide II.

Also exemplary of peptides suitable for the present invention are those described in U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529.

The non-peptide derivatives containing a hetero atom include, for example, heterocyclic compounds, in particular those containing sulfur, nitrogen or oxygen, and compounds comprising a nitrogen atom bonded directly or indirectly to a benzene ring.

Exemplary heterocyclic compounds according to the invention, for example those containing a nitrogen heterocycle, are described in EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116 and WO-A-94/08997. In particular, the compound comprising at least one nitrogen heterocycle is advantageously a 2-tricyclyl-2-aminoethane derivative, a spirolactam derivative, a quinuclidine derivative, an azacyclic derivative, an aminopyrrolidine derivative, a piperidine derivative, an aminoaza heterocycle or an isoindole derivative.

Other such heterocyclic compounds include the oxygen- or sulfur-containing heterocyclic compounds, such as furan derivatives, benzofuran derivatives, thiophene derivatives and benzothiophene derivatives, optionally containing nitrogenous substituents, such as the heterocyclic compounds described in U.S. Pat. No. 4,931,459, U.S. Pat. No. 4,910,317 and EP-A-299457, and, more especially, alkoxy- and/or aryloxytetrazolylbenzofurancarboxamides or alkoxy- and/or aryloxytetrazolylbenzothiophenecarboxamides.

Exemplary compounds containing a nitrogen atom bonded directly or indirectly to a benzene ring include those described in EP-A-552808, WO-A-93/01165 and WO-A-93/10073.

And exemplary salts include, in particular, strontium or lanthanide salts, and, for example, the chlorides, carbonates, borates, nitrates, acetates, hydroxides and sulfates, the fruit acid salts and the amino acid salts of strontium or of the lanthanides.

CGRP (calcitonin gene related peptide) is a polypeptide chemical compound produced and released by a nerve ending.

By "CGRP antagonist" is intended any substance or species of organic or inorganic origin capable of effecting an inhibition of the receptor binding of CGRP or of effecting an inhibition of the synthesis and/or release of CGRP by the sensory nerve fibers.

For a substance to be recognized as a CGRP antagonist, it must induce a coherent pharmacological response, in particular, in one of the following tests:

(a) the antagonist substance must decrease the vasodilation induced by capsaicin and/or by an antidromic electrical stimulation (applied to an afferent nerve), and/or (b) the antagonist substance must induce an inhibition of the release of CGRP by the sensory nerve fibers, and/or (c) the antagonist substance must inhibit the CGRP-induced contraction of the smooth muscle of the vas deferens.

Exemplary CGRP receptor antagonists include CGRP 8-37 (amino acid sequence 8 to 37 of the terminal end of CGRP), an anti-CGRP antibody, or an extract of plant origin.

Exemplary inflammation mediator antagonists which are suited for the invention include, in particular, histamine antagonists, interleukin-1 antagonists, cyclooxygenase antagonists and lipoxygenase antagonists.

The neuropeptide antagonists and the inflammation mediator antagonists are advantageously incorporated in an amount ranging from 0.000001% to 10% by weight relative to the total weight of the composition, and preferably from 0.0001% to 5%.

Thus, this invention also features cosmetic, pharmaceutical or dermatological compositions which comprise, in a cosmetically, pharmaceutically or dermatologically acceptable medium, at least one TNF-alpha antagonist and at least one neuropeptide antagonist and/or at least one inflammation mediator antagonist selected from among substance P antagonists, CGRP antagonists, cyclooxygenase antagonists and lipoxygenase antagonists.

The compositions according to the invention may be formulated in all forms suitable for topical application, in particular in the form of aqueous, aqueous-alcoholic or oily solutions, dispersions of the lotion or serum type, aqueous, anhydrous or oily gels, milk type emulsions of liquid or semi-liquid consistency obtained by dispersion of a fatty phase in an aqueous phase (O/W) or vice versa (W/O), cream or gel type suspensions or emulsions of soft, semi-solid or solid consistency, microemulsions or, alternatively, microcapsules, microparticles or vesicular dispersions of the ionic and/or nonionic type. These compositions are formulated according to standard techniques.

They may also be used for the hair in the form of aqueous, alcoholic or aqueous-alcoholic solutions, or in the form of creams, gels, emulsions or foams or, alternatively, in the form of aerosol compositions also containing a propellent under pressure.

The amounts of the various constituents of the compositions according to the invention are those conventionally used in the fields in question.

These compositions constitute, in particular, protective, treatment or care creams for the face, for the hands, for the feet, for the major anatomical folds or for the body, protective body milks or body care milks, lotions, gels or foams for care of the skin and the mucosae, as cleansing or disinfecting lotions, bath compositions and compositions containing a bactericidal agent.

The subject compositions may also be formulated as solid preparations constituting cleansing bars or soaps.

When the compositions of the invention are formulated as an emulsion, the proportion of the fatty phase advantageously ranges from 5% to 80% by weight, and preferably from 5% to 50% by weight, relative to the total weight of the composition. The oils, emulsifiers and coemulsifiers employed in the compositions in emulsion form are selected from among those traditionally used in the cosmetic, pharmaceutical or dermatological fields. The emulsifier and the coemulsifier are advantageously present in the subject compositions in a proportion ranging from 0.3% to 30% by weight, and preferably from 0.5% to 20% by weight, relative to the total weight of composition. The emulsion can, in addition, contain lipid vesicles.

When the composition is an oily solution or gel, the amount of oil can range up to more than 90% by weight of the total weight of the composition.

In known manner, the compositions of the invention may also contain additives and adjuvants which are conventional in the cosmetic, pharmaceutical and dermatological arts, such as hydrophilic or lipophilic gelling agents, hydrophilic or lipophilic active agents, preservatives, antioxidants, solvents, perfumes, fillers, screening agents, odor absorbers and colorants. The amounts of these various additives and adjuvants are those traditionally used in the fields in question, and range, for example, from 0.01% to 20% of the total weight of the composition. These additives and adjuvants, depending on their nature, may be introduced into the fatty phase, into the aqueous phase and/or into the lipid spherules.

Exemplary oils which are suitable for the compositions of the invention include mineral oils (liquid paraffin), vegetable oils (liquid fraction of shea butter, sunflower oil), animal oils (perhydrosqualene), synthetic oils (Purcellin oil), silicone oils (cyclomethicone) and fluorinated oils (perfluoro polyethers). Exemplary fats include the fatty alcohols, fatty acids (stearic acid) and waxes (paraffin, carnauba, beeswax).

Exemplary emulsifiers include, for example, glyceryl stearate, polysorbate 60 and the PEG-6/PEG-32/glycol stearate mixture marketed under the trademark Tefose® 63 by Gattefosse.

Exemplary solvents according to the invention include the lower alcohols, in particular ethyl alcohol and isopropanol.

Exemplary hydrophilic gelling agents which are suitable include carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, representative thereof are the modified clays such as bentones, the metal salts of fatty acids, such as aluminum stearates, hydrophobic silica, polyethylenes and ethylcellulose.

Exemplary hydrophilic active agents which may be incorporated include proteins or protein hydrolysates, amino acids, polyols, urea, allantoin, sugars and sugar derivatives, water-soluble vitamins, starch and bacterial or plant extracts, in particular of Aloe vera extracts.

And exemplary lipophilic active agents include tocopherol (vitamin E) and derivatives thereof, retinol (vitamin A) and derivatives thereof, essential fatty acids, ceramides and essential oils.

It is also intended, in addition, to combine the TNF-alpha antagonists with active agents intended, in particular, for the prevention and/or treatment of skin complaints, conditions and afflictions. Exemplary of these active agents are:

(1) Agents that modulate differentiation and/or proliferation and/or skin pigmentation, such as retinoic acid and isomers thereof, retinol and esters thereof, retinal, retinoids, in particular those described in FR-A-2,570, 377, EP-A-199636, EP-A-325540 and EP-A-402072, vitamin D and derivatives thereof, estrogens such as estradiol, kojic acid or hydroquinone;

(2) Antibacterials such as clindamycin phosphate, erythromycin or antibiotics of the tetracycline class;

(3) Antiparasitics, especially metronidazole, crotamiton or pyrethrinoids;

(4) Antifungals, especially compounds belonging to the imidazole class, such as econazole, ketoconazole or miconazole or salts thereof, polyene compounds such as amphotericin B, compounds of the allylamine family such as terbinafine, or, alternatively, octopirox;

(5) Steroidal anti-inflammatory agents such as hydrocortisone, anthraline (dioxyanthranol), anthranoids, betamethasone valerate or clobetasol propionate, or nonsteroidal anti-inflammatory agents such as ibuprofen and salts thereof, diclofenac and salts thereof, acetylsalicylic acid, paracetamol or glycyrrhetinic acid;

(6) Anaesthetic agents such as lidocaine hydrochloride and derivatives thereof;

(7) Antipruritic agents such as thenaldine, trimeprazine or cyproheptadine;

(8) Antiviral agents such as acyclovir;

(9) Keratolytic agents such as alpha- and beta-hydroxycarboxylic or beta-ketocarboxylic acids, their salts, amides or esters, and more especially hydroxy acids such as glycolic acid, lactic acid, malic acid, salicylic acid, citric acid and the fruit acids in general, and 5-n-octanoylsalicylic acid;

(10) Free radical scavengers such as alphatocopherol or esters thereof, superoxide dismutases, certain metal chelating agents or ascorbic acid and esters thereof;

(11) Antiseborrhoeics such as progesterone;

(12) Antidandruff agents such as octopirox or zinc pyrithione;

(13) Anti-acne agents such as retinoic acid or benzoyl peroxide;

(14) Antimetabolites;

(15) Agents for combating hair loss such as monoxidil;

(16) Antiseptics.

The cosmetic treatments of the invention may be carried out, in particular, by topically applying the hygiene or cosmetic compositions as described above according to the customary techniques. For example, application of creams, gels, serums, lotions or milks to the skin, scalp and/or mucosae.

In order to further illustrate the present invention and the advantages thereof, the following specific examples are given, it being understood that same are intended only as illustrative and in nowise limitative.

In said examples to follow, all parts and percentages are given by weight.

EXAMPLE 1

| Face cream (oil-in-water emulsion): | |
|---|---|
| Lisophylline | 0.5% |
| Glyceryl stearate | 2% |
| Polysorbate 60 (Tween 60 marketed by ICI) | 1% |
| Stearic acid | 1.4% |
| Triethanolamine | 0.7% |
| Carbomer | 0.4% |
| Cyclomethicone | 8% |
| Sunflower oil | 12% |
| Antioxidant | 0.05% |
| Preservative | 0.3% |
| Water | qs 100% |

EXAMPLE 2

| Emulsified gel (oil-in-water emulsion): | |
|---|---|
| Cyclomethicone | 3% |
| Purcellin oil (marketed by Dragoco) | 7% |
| PEG-6/PEG-32/glycol stearate (Tefose ® 63 marketed by Gattefosse) | 0.3% |
| Sulphasalazine | 0.3% |
| Preservative | 0.3% |
| Carbomer | 0.6% |
| Crotamiton | 5% |
| Glycyrrhetinic acid | 2% |
| Ethyl alcohol | 5% |
| Triethanolamine | 0.2% |
| Water | qs 100% |

EXAMPLE 3

| Face cream (oil-in-water emulsion): | |
|---|---|
| Lisophylline | 1% |
| Glyceryl stearate | 2% |
| Spantide | 0.5% |
| CGRP 8-37 | 0.25% |
| Polysorbate 60 (Tween 60 marketed by ICI) | 1% |
| Stearic acid | 1.4% |
| Triethanolamine | 0.7% |
| Carbomer | 0.4% |
| Cyclomethicone | 8% |
| Sunflower oil | 12% |
| Antioxidant | 0.05% |
| Preservative | 0.3% |
| Water | qs 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating neurogenic red skin blotches afflicting a human subject, comprising topically applying to said red skin blotches, for such period of time as is required to elicit a desired therapeutic/cosmetic response, a composition comprising an effective amount of at least one TNF-alpha antagonist.

2. A method for treating a rosacea condition afflicting a human subject, comprising topically applying to said rosacea condition, for such period of time as is required to elicit a desired response, a composition comprising an effective amount of at least one TNF-alpha antagonist.

3. The method as defined by claim 1 or 2, wherein said composition further comprises an organic or inorganic chemical species, or a plant or animal extract.

4. The method as defined by claim 3, wherein said at least one TNF-alpha antagonist is selected from the group consisting of lisophylline, A802715, sulphasalazine, CDP-571 (anti-TNF-alpha antibody) and MDL-201112.

5. The method as defined by claim 1 or 2, wherein said composition further comprises an effective amount of at least one agent selected from the group consisting of a neuropeptide antagonist, inflammation mediator antagonist, antibacterial agent, antiparasitic agent, antifungal agent, anti-inflammatory agent, antipruriginous agent, anaesthetic, antiviral agent, keratolytic agent, free radical scavenger, antiseborrhoeic agent, antidandruff agent, antiacne agent, and an active agent which modifies at least one of cutaneous differentiation, proliferation and pigmentation.

6. The method as defined by claim 5, wherein said at least one agent is selected from the group consisting of a neuropeptide antagonist and an inflammation mediator antagonist wherein said inflammation mediator antagonist is selected from the group consisting of substance P antagonists, CGRP antagonists, interleukin-1 antagonists, histamine antagonists, cyclooxygenase antagonists and lipoxygenase antagonists.

7. The method as defined by claim 1 or 2, wherein said composition further comprises at least one active agent selected from the group consisting of proteins or protein hydrolysates, amino acids, polyols, urea, allantoin, sugars, sugar derivatives, vitamins, starch, plant extracts, essential fatty acids, ceramides, essential oils and hydroxy acids.

8. The method of claim 1 or 2 wherein said composition further comprises a therapeutically or cosmetically acceptable, topically applicable carrier.

9. The method of claim 8 wherein said at least one TNF-alpha antagonist is in an amount ranging from 0.000001% to 10% by weight thereof.

10. The method of claim 9, wherein said at least one TNF-alpha antagonist is in an amount ranging from 0.0001% to 5% by weight thereof.

11. The method of claim 8, wherein said composition further comprises an organic or inorganic chemical species, or a plant or animal extract.

12. The method of claim 11, wherein said at least one TNF-alpha antagonist is selected from the group consisting of lisophylline, A802715, sulphasalazine, CDP-571 (anti-TNF-alpha antibody) and MDL-201112.

13. The method of claim 8 wherein said composition further comprises a therapeutically or cosmetically effective amount of at least one neuropeptide antagonist, inflammation mediator antagonist, antibacterial agent, antiparasitic agent, antifungal agent, anti-inflammatory agent, antipruriginous agent, anaesthetic, antiviral agent, keratolytic agent, free radical scavenger, antiseborrhoeic agent, antidandruff agent, antiacne agent, or an active agent which modifies at least one of cutaneous differentiation, proliferation and pigmentation.

14. The method of claim 8 wherein said composition further comprises at least one neuropeptide antagonist or inflammation mediator antagonist, wherein said inflammation mediator antagonist is selected from the group consisting of substance P antagonists, CGRP antagonists, interleukin-1 antagonists, histamine antagonists, cyclooxygenase antagonists and lipoxygenase antagonists.

15. The method of claim 13, wherein said active agent is in an amount ranging from 0.000001% to 10% by weight thereof.

16. The method of claim 8 wherein said composition further comprises at least one active agent selected from the group consisting of proteins, protein hydrolysates, amino acids, polyols, urea, allantoin, sugars, sugar derivatives, vitamins, starch, plant extracts, essential fatty acids, ceramides, essential oils and hydroxy acids.

17. The method of claim 8 wherein said composition further comprises an aqueous, oily or aqueous-alcoholic solution, an oil-in-water or water-in-oil emulsion, a microemulsion, an aqueous or anhydrous gel, a serum, or a dispersion of vesicles, microcapsules or microparticles.

18. The method of claim 8 wherein said composition is in the form of a gel, cream, lotion, milk or foam.

19. The method as defined by claim 1, wherein said composition is applied to the skin, scalp and/or mucosae of said human subject.

20. The method as defined by claim 2, wherein said composition is applied to the skin, scalp and/or mucosae of said human subject.

* * * * *

UNITED STATES PATENT AND TRADEMARK OFFICE
CERTIFICATE OF CORRECTION

PATENT NO. : 5,895,649
DATED : April 20 1999
INVENTOR(S) : Olivier DE LACHARRIERE et al.

It is certified that error appears in the above-identified patent and that said Letters Patent is hereby corrected as shown below:

At Column 4, line 34, please change "must induce an inhibition" to --must reduce an inhibition--.

Signed and Sealed this

Twenty-first Day of November, 2000

Attest:

Q. TODD DICKINSON

Attesting Officer     Director of Patents and Trademarks